(12) United States Patent
Gers-Barlag et al.

(10) Patent No.: US 7,037,511 B1
(45) Date of Patent: *May 2, 2006

(54) HYDROUS COSMETIC OR PHARMACEUTICAL STICKS

(75) Inventors: Heinrich Gers-Barlag, Kummerfeld (DE); Anja Müller, Rümpel (DE); Xenia Petsitis, Hofheim (DE); Ghita Lanzendörfer, Hamburg (DE); Melanie Kovacevic, Hamburg (DE)

(73) Assignee: Beiersdorf AG, Hamburg (DE)

( * ) Notice: Subject to any disclaimer, the term of this patent is extended or adjusted under 35 U.S.C. 154(b) by 365 days.

This patent is subject to a terminal disclaimer.

(21) Appl. No.: 09/640,822

(22) Filed: Aug. 17, 2000

(30) Foreign Application Priority Data

Aug. 21, 1999 (DE) .................................. 199 39 835

(51) Int. Cl.
- A61K 6/00 (2006.01)
- A61K 7/00 (2006.01)
- A61K 9/70 (2006.01)
- A61K 7/42 (2006.01)

(52) U.S. Cl. ..................... 424/401; 424/449; 424/59; 424/64; 514/770; 514/744

(58) Field of Classification Search ................ 424/401, 424/489, 59, 64, 78.03, 449; 514/770, 844, 514/937, 953, 744
See application file for complete search history.

(56) References Cited

U.S. PATENT DOCUMENTS

| | | | |
|---|---|---|---|
| 4,446,051 A | 5/1984 | Berthod | |
| 4,814,165 A | 3/1989 | Berg et al. | 424/63 |
| 5,015,469 A * | 5/1991 | Yoneyama et al. | 424/59 |
| 5,182,103 A | 1/1993 | Nakane et al. | 424/78.03 |
| 5,302,280 A | 4/1994 | Lomas et al. | 208/113 |
| 5,622,993 A | 4/1997 | McGinity et al. | 514/626 |
| 5,690,916 A | 11/1997 | Kimura et al. | 424/59 |
| 5,804,167 A * | 9/1998 | Schonrock et al. | 424/59 |
| 5,853,711 A * | 12/1998 | Nakamura et al. | 424/78.03 |
| 5,939,054 A * | 8/1999 | Msika et al. | 424/59 |
| 6,022,530 A * | 2/2000 | Gers-Barlag et al. | 424/59 |
| 6,080,430 A * | 6/2000 | Ogawa et al. | 424/490 |
| 6,153,204 A * | 11/2000 | Fanger et al. | 424/401 |

FOREIGN PATENT DOCUMENTS

JP 8217619 8/1996

OTHER PUBLICATIONS

Product Literature for Bentone 38, May 11, 1999.
Product Literature for Bentone 27, Dec. 20, 1996.
U.S. Appl. No. 09/455,230, filed Dec. 6, 1999, Gers-Barlag et al.
U.S. Appl. No. 09/641,013, filed Aug. 17, 2000, Gers-Barlag et al.
U.S. Appl. No. 09/640,528, filed Aug. 17, 2000, Gers-Barlag et al.
U.S. Appl. No. 09/744,642, filed Jan. 26, 2001, Gers-Barlag et al.

* cited by examiner

Primary Examiner—Shaojia Anna Jiang
(74) Attorney, Agent, or Firm—Norris Mclaughlin & Marcus P.A.

(57) ABSTRACT

Cosmetic or dermatological stick preparations, which are finely disperse systems of the water-in-oil type, comprising
a) an oil phase which comprises from 10 to 70% by weight, based on the weight of the fatty phase, of fatty and/or wax components which melt above a temperature of 40° C.,
b) a water phase,
c) at least one modified phyllosilicate which exhibits both hydrophilic and also lipophilic properties, which thus has amphiphilic character and positions itself at the water/oil interface, and
d) at most 0.5% by weight of one or more emulsifiers and method for their preparation.

16 Claims, No Drawings

HYDROUS COSMETIC OR PHARMACEUTICAL STICKS

The present invention relates to cosmetic or pharmaceutical sticks which are in the form of W/O emulsions and which are characterized by an increased water content. In particular, the invention relates to decorative lipsticks and lipcare sticks, but also to deodorizing or antiperspirant sticks, and to stick formulations which are suitable, for example, for use against acne. As further advantageous embodiments, the present invention relates to sunscreen sticks and so-called make-up or cosmetic sticks, such as, for example, eyebrow pencils, kohl pencils, eyeshadow pencils, eyeliner pencils, concealer sticks, powder sticks and comparable products.

In cosmetics, there are predominantly three fields of application for stick formulations: the fields of lipcare and deodorants and the field of cosmetic sticks, which are a particular application form of make-up preparations.

Lipsticks nowadays include two product classes: conventional lipsticks, which primarily serve to colour the lips, and mostly colourless care sticks, which are used either for greasing the lips or for sun protection.

The skin of the lips has only an extremely thin horny layer. There are no sweat glands on the lips, and only a few sebaceous glands. The skin on the lips is therefore virtually free from lipids and is prone to drying out, particularly in cold and dry weather. It is possible for small cracks to form in the skin, and the susceptibility of the lips to chemical, physical and microbial factors (e.g. foods, sunlight, Herpes simplex viruses) increases.

One purpose of lipcare sticks is to prevent this. These products usually contain a high proportion of waxes and fatty components which form a covering layer on the lips following application.

It is possible to additionally incorporate into care stick preparations active ingredients which care for or protect the lips, such as, for example, vitamins, light protection agents, covering pigments etc.

In contrast, decorative lipsticks contain many different colour pigments. The dyes are primarily chosen with the aim of achieving a shade of colour which is currently fashionable. In this connection, however, it must be observed that all dyes and pigments for lipsticks are subject to legal provisions with respect to their use, in Germany, for example, the directive on cosmetic products. Lipsticks are among the most used decorative cosmetic products. Their practical form permits repeated application and restoration of the colour and of the protective film throughout the day.

Decorative lipsticks also comprise high proportions of waxes and fatty components which, following application, form a covering lipid layer over the lips. This lipid layer serves as a base, which adheres to the lips, for the incorporated dyes, since the latter, for various reasons, cannot be applied to the lips without such a base.

It is also possible to combine the properties of the care and decorative lipsticks with one another, i.e. to incorporate care or protective substances in decorative lipsticks.

High requirements are placed on a good lipstick with regard to its quality. These are firstly application properties, but secondly also legal provisions which, for example, govern the use of dyes.

The consumer expects a lipstick to have a clean, smooth and glossy surface. In addition, neither oil droplets nor wax crystals should settle out. Application must also be possible without problems. In particular, it should be possible to apply lipstick smoothly and without large frictional resistance. Even when pressed lightly, the stick should produce a well-adhering fatty film on the lips. The film achieved must cover the lips well, stay on for as long as possible and not be sticky, and also impart shine to the lips. Moreover, lipsticks should be unbreakable and temperature-resistant, and the formulations must not lose oil. In addition, for decorative lipsticks, high adhesive strength of the colour on the lips is desirable, i.e. they should colour the lips intensely and such that they cannot be wiped off easily.

Many make-up formulations, such as, for example, eyebrow and kohl pencils etc., are also supplied in the form of sticks—for example in the style of lead pencils. For defining and colouring eyebrows, use is usually made of formulations in which the colouring pigments are incorporated in a wax/oil base. The finished dye/wax composition is generally extruded as lead and formulated into pencils made of red cedarwood. In principle, the consumer places the same requirement on decorative eyecare pencils as on corresponding lipcare products.

A common feature of all decorative cosmetics is that they comprise greater or lesser amounts of dyes or colour pigments. The dyes can be present as constituents of true solutions, or in the form of pigment dispersions. The combination of soluble dyes with insoluble pigments is also used. The base of decorative cosmetics can be very different, but although in principle all possibilities are available, anhydrous, lipophilic systems are mainly chosen as bases.

In contrast, a deodorant stick or an antiperspirant stick is expected not only to be effective, but, in particular, not to produce a greasy feel when applied to the underarms.

If cosmetic or pharmaceutical sticks are to contain certain active ingredients, it is conceivable for the other constituents to be incompatible with the active ingredients. This is often the case particularly when the intention is to use the cosmetic sticks as deodorant sticks. Antiperspirant sticks usually contain, for example, aluminium chlorohydrate, which is a strong Lewis acid and cannot be used for many of the stick formulations.

From a technical point of view there are, in particular, two ways of formulating sticks which are of particular importance:

Anhydrous fatty mixtures of solid or semisolid waxes and liquid oils are generally used as lipstick bases and in the field of make-up sticks. Customary prior art bases for stick preparations of this type are, for example, liquid oils (e.g. paraffin oils, castor oil, isopropyl myristate), semisolid constituents (e.g. Vaseline, lanolin), solid constituents (e.g. beeswax, ceresin and microcrystalline waxes or ozokerite) and high-melting waxes (e.g. carnauba wax, candelilla wax). In the field of lipcare, however, hydrous preparations are also known, which are sometimes also in the form of W/O emulsions. Necessary ingredients of emulsion stick preparations of the prior art are emulsifiers, such as, for example, polyglyceryl-3 diisostearate or polyglyceryl-3 oleate (EP-600 931-B2 and EP617 952-B2) or lecithin (EP-522 624-A1). Such stick formulations are generally characterized by a water content of markedly less than 10% by weight.

Lipsticks, kohl pencils and eyebrow pencils of the prior art containing paraffins and beeswax or japan wax are described in "*Kosmetik, Entwicklung Herstellung und Anwendung kosmetischer Mittel*" [Cosmetics, Development Preparation and Use of Cosmetic Compositions], Editor: W. Umbach, Georg Thieme Verlag, Stuttgart—New York, 1995, p. 321 ff.

By contrast, the bases used for deodorizing sticks are generally soap/glycol gels. These form when lower glycols and glycerol, in the presence of sodium stearate, form clear, transparent gels which can additionally absorb alcohol and water. However, such formulations are incompatible with aluminium chlorohydrate.

The prior art has a number of disadvantages. These include the fact that lipophilic stick formulations can usually comprise only a very small amount of water since otherwise the stick consistency is lost. Since water-soluble active ingredients are generally insufficiently soluble in fats, they cannot be incorporated into lipophilic cosmetic bases to any significant extent. However, a certain water content is certainly required in a stick formulation, including in particular to increase the compatibility of the stick with the human skin. However, because water is incompatible with the hydrophobic oil/wax/emulsifier matrix, sticks with high water contents cannot be made in accordance with the prior art.

An object of the present invention was to overcome these shortcomings.

A further object of the present invention was to develop preparations which are suitable as bases for cosmetic deodorants and antiperspirants and do not have the disadvantages of the prior art and which are further characterized by good skin compatibility.

Since the skin in the lip area is virtually completely devoid of pigments, it is extremely sensitive to ultraviolet radiation. It is therefore advisable to apply to the lip area special protection against UV radiation in the form of suitable stick light protection preparations, particularly in conditions of increased UV exposure, such as, for example, in high mountains. Even in stick preparations of the prior art, therefore, inorganic pigments are often used as UV absorbers or UV reflectors to protect the lip area against UV rays. These are, in particular, oxides of titanium, but also occasionally of zinc, iron, zirconium, silicon, manganese, aluminium, cerium and mixtures thereof, and modifications.

A significant shortcoming of the prior art formulations is, however, that, because of the low water contents of emulsion sticks acceptable per se, it was virtually impossible to incorporate water-soluble UV filter substances into such formulations. A further object of the present invention was thus also to overcome this shortcoming.

DBP 23 35 549 discloses a method for the preparation of a cosmetic stick based on a W/O emulsion. According to this teaching, a polyhydroxy compound and a nonionogenic, surface-active compound are used to prepare a gel, which is mixed with a cosmetic base, and water is emulsified into the mixture.

However, this method cannot be used to prepare sticks which have the universally applied requirements of a cosmetic stick. Moreover, since this method is not a one-step method, it is characterized by further disadvantages.

DE-A 41 28 748 describes cosmetic sticks which are characterized in that they are emulsions and comprise, as essential constituents, beeswax, one or more esters of a saturated carboxylic acid having 20–40 carbon atoms and a saturated alcohol having 14–34 carbon atoms, water and optionally further lipids and/or customary auxiliaries and additives. Although these preparations do have advantageous properties, the effect achieved still falls some way short of the desired effect.

Emulsions are by far the most important product type in the field of skincare products. Emulsions are dispersed two- or multi-phase systems, cosmetic emulsions consisting of at least one fatty phase (fats and mineral oils, fatty acid esters, fatty alcohols etc.) and at least one water phase (water, glycerol, glycols etc.), which are finely distributed in one another using emulsifiers.

In order to achieve the permanent dispersion of one liquid in another, in the case of emulsions in the traditional sense, the addition of an interface-active substance (emulsifier) is necessary. Emulsifiers have an amphiphilic molecular structure, consisting of a polar (hydrophilic) and a nonpolar (lipophilic) molecular moiety, which are spatially separate from one another. In simple emulsions, finely disperse droplets of one phase (water droplets in W/O emulsions or lipid vesicles in O/W emulsions), surrounded by an emulsifier shell, are present in a second phase. Emulsifiers reduce the interfacial tension between the phases by positioning themselves at the interface between the two liquids. At the oil/water phase boundary they form interfacial films, which prevent irreversible coalescence of the droplets. Emulsions are frequently stabilized using emulsifier mixtures.

Depending on their hydrophilic molecular moiety, traditional emulsifiers can be categorized into ionic (anionic, cationic and amphoteric) and nonionic:

The best-known example of an anionic emulsifier is soap, a term usually used to refer to the water-soluble sodium or potassium salts of saturated or unsaturated higher fatty acids.

The quaternary ammonium compounds are important representatives of cationic emulsifiers.

The hydrophilic molecular moiety of nonionic emulsifiers often consists of glycerol, polyglycerol, sorbitans, carbohydrates or polyoxyethylene glycols and is usually linked to the lipophilic molecular moiety via ester and ether bonds. The lipophilic molecular moiety usually consists of fatty alcohols, fatty acids or isofatty acids.

By varying the structure and the size of the polar and of the nonpolar molecular moiety, the lipophilicity and hydrophilicity of emulsifiers can be varied within wide limits.

A decisive factor for the stability of a (traditional) emulsion is the correct choice of emulsifiers. Here, the characteristics of all substances present in the system are to be taken into account. If, for example, skincare emulsions are considered, then polar oil components and, for example, UV filters lead to instability. As well as the emulsifiers, therefore, other stabilizers are generally also used which, for example, increase the viscosity of the emulsion and/or act as protective colloid.

The use of customary emulsifiers in cosmetic or dermatological preparations is not questionable per se. Nevertheless, emulsifiers, like ultimately any chemical substance, may, in individual cases, cause allergic reactions or reactions based on hypersensitivity of the user.

Thus, for example, it is known that certain light dermatoses are triggered by certain emulsifiers, but also by a variety of fats and simultaneous exposure to sunlight. Such light dermatoses are also called "Mallorca acne". There has thus been no lack of attempts to reduce the amount of customary emulsifiers to a minimum, ideally even completely.

A reduction in the required amount of emulsifier can, for example, be achieved by taking advantage of the fact that very finely divided solid particles have an additionally stabilizing action. This leads to an accumulation of the solid substance at the oil/water phase-boundary in the form of a layer, as a result of which coalescence of the disperse phases is prevented. The solid particles form, so to speak, a mechanical barrier against the combining of the liquid droplets at the interface between the two liquid phases.

One way of achieving solids stabilization in a cosmetic or dermatological preparation is, according to May-Alert (*Pharmazie in unserer Zeit* [Pharmacy in our Time], Vol. 15, 1986, No. 1, 1–7), for example, to use emulsifier mixtures which comprise both anionic and cationic surfactants. Since mixing anionic and cationic surfactants produces precipitates of insoluble, electroneutral compounds, deliberate precipitation of these neutral surfactants in the oil/water interface makes it possible to achieve additional solids stabilization. However, these emulsions have the disadvantage that the amount of customary emulsifiers is not actually reduced.

Emulsions which are (additionally) stabilized by solids are also referred to as Pickering emulsions after their original inventor.

Pickering emulsions of the prior art—like traditional emulsions—cannot be formulated as sticks since they are in liquid or, at best, viscous form. They are therefore used in the field of skincare, for example as skin or face cream, cleansing milk, protection lotion, nourishing cream and the like.

A further object of the present invention was therefore to enrich the prior art with cosmetic or pharmaceutical stick formulations which are in the form of W/O emulsions and which are characterized by an increased water content.

Surprisingly, all of these objects are achieved by cosmetic or dermatological stick preparations, which are finely disperse systems of the water-in-oil type, comprising
1. an oil phase which comprises from 10 to 70% by weight, based on the weight of the fatty phase, of fatty and/or wax components which melt above a temperature of 40° C.,
2. a water phase,
3. at least one modified phyllosilicate which exhibits both hydrophilic and lipophilic properties, which thus has amphiphilic character and positions itself at the water/oil interface, and
4. at most 0.5% by weight of one or more emulsifiers, and optionally comprising further cosmetic or pharmaceutical auxiliaries, additives and/or active ingredients.

It is particularly advantageous according to the invention if the stick preparations comprise markedly less than 0.5% by weight of one or more emulsifiers. Very particular preference is given to preparations according to the invention which are entirely free from emulsifiers in the traditional sense.

The amphiphilic character of the modified phyllosilicate particles according to the invention is evident, for example, from the fact that they are dispersible both in water and in oil.

The preparations according to the invention are mixtures of oils or oil-soluble substances and water or water-soluble components which are stabilized by the addition of the micronized solid particles and do not contain an emulsifier in the traditional sense.

The preparations according to the invention are extremely satisfactory preparations in every respect, whose water/fatty phase ratio is surprisingly extremely variable. It was particularly surprising that the stick preparations according to the invention can have a significantly increased water content compared with the prior art. They are characterized by excellent cosmetic properties and therefore suitable for use in many areas of care and decorative cosmetics. For many applications, it is particularly advantageous that the preparations according to the invention are free from emulsifiers in the traditional sense. The preparations according to the invention are also excellent vehicles for a wide variety of active ingredients.

The water phase content of the formulations according to the invention is preferably chosen from the range from 5 to 80% by weight, particularly advantageously from the range 10 to 70% by weight, in particularly 15 to 60% by weight, in each case based on the total weight of the formulations.

Modified Phyllosilicates

Silicates are salts and esters (silicic esters)—of orthosilicic acid [Si(OH)$_4$] and condensation products thereof. Silicates are not only the class of minerals which contain the most types, but are also extremely important from a geological and industrial viewpoint. Over 80% of the earth's crust consists of silicates. Phyllosilicates are (ideally) silicate structures having two-dimensionally infinite layers of [SiO$_4$]$^{4-}$ tetrahedra, each tetrahedron being bonded to neighbouring tetrahedra by 3 bridging oxygens.

Only approximate chemical formulae can be given for phyllosilicates since they have a large ion-exchange ability, and silicon can be replaced by aluminium, and this in turn can be replaced by magnesium, Fe$^{2+}$, Fe$^{3+}$, Zn and the like. The negative charge of the layers which may result is usually balanced by cations, in particular by Na$^+$ and Ca$^{2+}$ in interlayer positions.

Phyllosilicates can swell by reversible intercalation of water (in a 2- to 7-fold amount) and other substances, such as, for example, alcohols, glycols and the like. Their use as thickeners in cosmetic compositions is, accordingly, known per se. However, the prior art was unable to point the way to the present invention.

Advantageous phyllosilicates for the purposes of the present invention are, for example, those whose greatest expansion direction in the unmodified and unswollen state has, on average, a length of less than 10 μm. For example, the average expansions of the modified phyllosilicate particles used can be 1000 nm×100 nm×1 nm and below. The effective size of the modified phyllosilicate particles in a cosmetic or dermatological formulation naturally depends on the amount of intercalated substances.

Advantageous modified phyllosilicates for the purposes of the present invention are, for example, modified smectites.

Smectites are always very finely particulate (in most cases <2 mm) three-layer clay minerals (2:1 phyllosilicates) which occur mainly as lamella-shaped, moss-like or spherical aggregates, in which a central layer of octahedrally coordinated cations is sandwiched by two layers of [(Si,Al)O$_4$] tetrahedra. Smectites are described in an idealized manner by the following structural formula, in which circles filled in white are silicon and/or aluminium atoms, circles filled in pale grey are oxygen atoms, circles filled in dark grey are hydrogen atoms, and circles filled in black are aluminium, magnesium, iron atoms and/or other exchange cations:

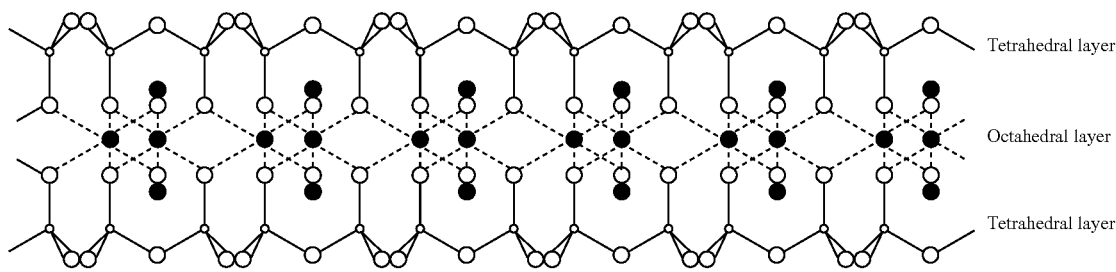

Advantageous modified smectites are, for example, modified montmorillonites. Montmorillonites are described by the approximate chemical formula $Al_2[(OH)_2/Si_4O_{10}]\cdot n\ H_2O$ or $Al_2O_3\cdot 4\ SiO_2H_2O\cdot n\ H_2O$, and are clay minerals belonging to the dioctahedral smectites.

Also particularly advantageous for the purposes of the present invention are, for example, modified hectorites. Hectorites belong to the smectites and have the approximate chemical formula $M^+{}_{0.3}(Mg_{2.7}Li_{0.3})[Si_4O_{10}(OH)_2]$, in which $M^+$ is in most cases $Na^+$.

Also advantageous for the purposes of the present invention are modified bentonites. Bentonites are clays and rocks which contain smectites, especially montmorillonite, as main minerals. The "crude" bentonites are either calcium bentonites (referred to in Great Britain as fuller's earth) or sodium bentonites (also: Wyoming bentonites).

Modified phyllosilicates for the purposes of the present invention are phyllosilicates, in particular the phyllosilicate types already mentioned, whose organophilicity (also: lipophilicity) has been increased, for example by reaction with quaternary ammonium compounds. Such phyllosilicates are also referred to as organophilic phyllosilicates.

Particularly advantageous for the purposes of the present invention are bentones, i.e. organic derivatives of montmorillonites (or bentonites) and/or hectorites, which are prepared by ion-exchange reactions with alkylammonium bases.

Advantageous modified phyllosilicates for the purposes of the present invention are obtainable, for example, by reacting phyllosilicates with quaternium-18. Quaternium-18 is a mixture of quaternary ammonium chloride salts which are described by the following structural formula:

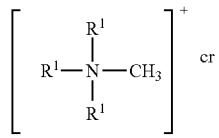

in which the radicals $R^1$ are chosen independently of one another from the group consisting of methyl and hydrogenated tallow radicals having a chain length of from 12 to 20 carbon atoms.

According to the invention, particular preference is given to stearalkonium hectorite, a reaction product of hectorite and stearalkonium chloride (benzyldimethylstearyl-ammonium chloride), and quaternium-18 hectorite, a reaction product of hectorite and quaternium-18, which are available, for example, under the trade names Bentone 27 and Bentone 38 from Nordmann & Rassmann.

The total amount of one or more modified phyllosilicates in the finished cosmetic or dermatological preparations is advantageously chosen from the range 0.05 to 10.0% by weight, preferably 0.1 to 5.0% by weight, based on the total weight of the preparations.

Although it is particularly preferred to stabilize the preparations according to the invention only by the addition of one or more modified phyllosilicates, it may also be advantageous to combine the modified phyllosilicate particles with other amphiphillic pigments which can, where appropriate, also contribute to the stabilization of the Pickering emulsion sticks.

Such pigments are, for example, micronized, inorganic pigments which are chosen from the group of amphiphilic metal oxides, in particular from the group consisting of titanium dioxide, zinc oxide, silicon dioxide or silicates (e.g. talc, kaolin), where the metal oxides can be present either individually or in a mixture. In this connection, it is essentially unimportant in which of the potentially naturally occurring modifications the amphiphilic metal oxides used are present.

It is advantageous to choose the average particle diameter of the pigments used for the combination with modified phyllosilicates to be between 1 nm and 200 nm, particularly advantageously between 5 nm and 100 nm.

It is advantageous for the purposes of the present invention to combine the modified phyllosilicates according to the invention with untreated, virtually pure pigment particles, in particular with those which can also be used as dye in the foods industry and/or as absorbers of UV radiation in sunscreens. Examples of advantageous pigments are the zinc oxide pigments obtainable from Merck and those obtainable under the trade names Zinkoxid neutral from Haarmann & Reimer or NanoX from Harcros Chemical Group.

Also advantageous according to the invention is the combination of modified phyllosilicates with inorganic pigments which have been surface-treated to repel water ("coated"), the intention being for the amphiphilic character of these pigments to be simultaneously formed or retained. This surface treatment may involve providing the pigments with a thin hydrophobic layer by processes known per se.

One such process, which is described below using titanium dioxide as an example, consists in, for example, producing the hydrophobic surface layer according to the following reaction

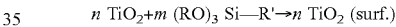

n and m are arbitrary stochiometric parameters, and R and R' are the desired organic radicals. Particularly advantageous combination partners are $TiO_2$ pigments, for example those coated with aluminium stearate and obtainable under the trade name MT 100 T from TAYCA.

A further advantageous coating of the combination partners consists of dimethylpolysiloxane (also: dimethicone), a mixture of fully methylated, linear siloxane polymers which are terminally blocked with trimethylsiloxy units. Particularly advantageous for the purposes of the present invention is the combination of modified phyllosilicates with zinc oxide pigments which have been coated in this way.

It is also advantageous when the inorganic pigments used alongside modified phyllosilicates are coated with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments are additionally coated with aluminium hydroxide or aluminium oxide hydrate (also: alumina, CAS No.: 1333-84-2). Particularly advantageous combination partners are titanium dioxides coated with simethicone and alumina, it being possible for the coating to also contain water. One example thereof is the titanium dioxide obtainable under the trade name Eusolex T2000 from Merck.

Also advantageous for the purposes of the present invention is the combination of modified phyllosilicates with a mixture of different inorganic, amphiphilic pigment types either within one crystal, for example as an iron mixed oxide or talc (magnesium silicate), or else by mixing two or more types of metal oxide within a preparation. Particularly advantageous combination partners are magnesium silicates, for example those obtainable under the trade name Talkum Micron from Grolmann.

The modified phyllosilicates according to the invention can also be advantageously combined with further pigments, for example with titanium dioxide pigments coated with octylsilanol, and/or with silicon dioxide particles which have been surface-treated to repel water. Silicon dioxide particles which are suitable for the combination are, for example, spherical polyalkylsilsesquioxane particles, as mentioned in European laid-open specification 0 686 391. Such polyalkylsilsesquioxane particles are obtainable, for example, under the trade names Aerosil R972 and Aerosil 200V from Degussa.

The modified phyllosilicates are further advantageously combined with microfine polymer particles which are present in the preparation in the form of solids. Favourable combination partners for the purposes of the present invention are, for example, polycarbonates, polyethers, polyethylene, polypropylene, polyvinyl chloride, polystyrene, polyamides, polyacrylates and the like.

Combination partners which are suitable according to the invention are, for example, microfine polyamide particles, in particular those obtainable under the trade name SP-500 from TORAY. Also advantageous are polyamide 6- (also: Nylon 6) and polyamide 12 (also: Nylon 12) particles. Polyamide 6 is the polyamide formed from ε-aminocaproic acid (6-aminohexanoic acid) or ε-caprolactam [poly(ε-caprolactam)], and polyamide 12 is a poly (ε-laurinlactam) from ε-laurinlactam. For the purposes of the present invention, Orgasol® 1002 (polyamide 6) and Orgasol® 2002 (polyamide 12) from ELF ATOCHEM, for example, are advantageous.

Other advantageous microfine polymer particles which are suitable for combination with the modified phyllosilicates according to the invention are microfine polymethacrylates. Such particles are obtainable, for example, under the trade name POLYTRAP® from DOW CHEMICAL.

It is particularly advantageous, but not obligatory, if the microfine polymer particles used as combination partners have been surface-coated. This surface treatment can consist in providing the polymer particles with a thin hydrophilic layer by methods known per se. Advantageous coatings consist, for example, of titanium dioxide (TiO$_2$), zirkonium dioxide (ZrO$_2$) or else other polymers, such as, for example, polymethyl methacrylate. Particularly advantageous microfine polymer particles for the purposes of the present invention are, for example, those obtainable by the process for the hydrophilic coating of hydrophobic polymer particles described in U.S. Pat. No. 4,898,913.

The average particle diameter of the microfine polymer particles used as combination partners is preferably chosen to be less than 100 µm, particularly advantageously less than 50 µm. In this connection, it is essentially unimportant in which form (platelets, rods, spherules etc.) the polymer particles used are present.

The modified phyllosilicates according to the invention are also advantageously combined with amphiphilic modified polysaccharides which do not exhibit thickening properties.

Such amphiphilic polysaccharides are obtainable, for example, by reacting starch with mono-, bi- or polyfunctional reagents or oxidizing agents in reactions which proceed in a largely polymer-analogous manner.

These reactions are based essentially on modifications of the hydroxyl groups of the polyglucans by etherification, esterification or selective oxidation. This produces, for example, starch ethers and starch esters of the general structural formula

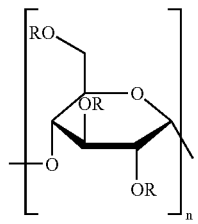

in which R can, for example, be a hydrogen and/or an alkyl radical and/or aralkyl radical (in the case of starch ethers) or a hydrogen and/or an organic and/or inorganic acid radical (in the case of starch esters). Starch ethers and starch esters are advantageous combination partners for the purposes of the present invention.

It is particularly advantageous to combine the modified phyllosilicates according to the invention with starch ethers, e.g. with those obtainable by etherifying starch with tetramethylolacetylenediurea and which are referred to as Amylum non mucilaginosum (non-swelling starch).

Also particularly advantageous is the combination of modified phyllosilicates according to the invention with starch esters and/or salts thereof, for example with sodium and/or aluminium salts of half-esters of starch which have low degrees of substitution, in particular with sodium starch n-octenyl succinate of the structural formula (I), in which R is characterized by the following structure

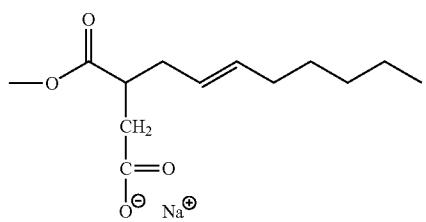

and which is available, for example, under the trade name Amiogum® 23 from CERESTAR, and with aluminium starch octenyl succinate, in particular with those obtainable under the trade names Dry Flo® Elite LL and Dry Flo® PC from National Starch & Chemical.

It is advantageous to choose the average particle diameter of the modified polysaccharides used for the combination with the phyllosilicates modified according to the invention to be less than 20 µm, particularly advantageously less than 15 µm.

The list of said modified polysaccharides which can be combined with the modified phyllosilicates is of course not intended to be limiting. Modified polysaccharides which are advantageous combination partners for the purposes of the present invention are obtainable in numerous ways known per se, either of a chemical or a physical nature. For the preparation of such polysaccharides, in principle novel ways are also conceivable. In this connection, it is essential that the modified polysaccharides exhibit amphiphilic properties and that they do not have a thickening action.

The modified phyllosilicates according to the invention are also preferably combined with boron nitride.

Advantageous combination partners for the purposes of the present invention are, for example, the boron nitrides listed below:

| Trade name | available from: |
| --- | --- |
| Boron Nitride Powder | Advanced Ceramics |
| Boron Nitride Powder | Sintec Keramik |
| Ceram Blanche | Kawasaki |
| HCST Boron Nitride | Stark |
| Très BN ® | Carborundum |
| Wacker-Bornitrid BNP | Wacker-Chemie |

It is advantageous to choose the average particle diameter of the boron nitride particles used to be less than 20 μm, particularly advantageously less than 15 μm.

Likewise advantageous combination partners are boron nitride particles which have been surface-treated to repel water ("coated"), the intention being for the amphiphilic character to be simultaneously formed or retained.

An advantageous coating of the boron nitride particles consists of dimethylpolysiloxane (also: dimethicone), a mixture of fully-methylated, linear siloxane polymers which have been terminally blocked with trimethylsiloxy units. Advantageous boron nitride particles treated with dimethicone are, for example, those available from Carborundum under the trade name Très BN® UHP 1106.

Also advantageous is a coating of the boron nitride particles with polymethylhydrogensiloxane, a linear polysiloxane which is also referred to as methicone. Examples of advantageous boron nitride particles coated with methicone are those obtainable from Carborundum under the trade name Très BN® UHP 1107.

In all of the above cases, it is advantageous to choose the total concentration of all pigments to be greater than 0.05% by weight, particularly advantageously between 0.05% by weight and 30% by weight, based on the total weight of the preparations, where the concentration of modified phyllosilicates—likewise based on the total weight of the preparations—for the purposes of the present invention is advantageously chosen from the range 0.05% by weight to 10% by weight, advantageously 0.1% by weight to 5% by weight.

Waxes

According to the invention, the high-melting fatty and/or wax components are advantageously chosen from the group of vegetable waxes, animal waxes, mineral waxes and petrochemical waxes. According to the invention, favourable examples are candelilla wax, carnauba wax, japan wax, esparto grass wax, cork wax, guaruma wax, rice germ oil wax, sugar cane wax, berry wax, ouricury wax, montan wax, jojoba wax, shea butter, beeswax, schellack wax, spermaceti, lanolin (wool wax), uropygial wax, ceresin, ozokerite (earth wax), paraffin waxes and microcrystalline waxes.

Other advantageous fatty and/or wax components are chemically modified waxes and synthetic waxes, such as, for example, those obtainable under the trade names Syncrowax HRC (glyceryl tribehenate), Syncrowax HGLC ($C_{16-38}$-fatty acid triglyceride) and Syncrowax AW 1C ($C_{18-38}$-fatty acid) from CRODA GmbH, and also montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Also advantageous are certain organosilicon compounds which have similar physical properties to said fatty and/or wax components, such as, for example, stearoxytrimethylsilane.

According to the invention, the fatty and/or wax components can be present either individually or as a mixture.

The Pickering emulsion sticks according to the invention can advantageously also comprise thickeners, in particular oil thickeners, in order to improve the tactile properties of the emulsion and the stick consistency. Advantageous oil thickeners for the purposes of the present invention are, for example, other solids, such as, for example, hydrophobic silicon oxides of the Aerosil® type, which are obtainable from Degussa AG. Advantageous Aerosil® types are, for example, Aerosil® OX50, Aerosil® 130, Aerosil® 150, Aerosil® 200, Aerosil® 300, Aerosil® 380, Aerosil® MOX 80, Aerosil® MOX 170, Aerosil® COK 84, Aerosil® R 202, Aerosil® R 805, Aerosil® R 812, Aerosil® R 972, Aerosil® R 974 and/or Aerosil® R976.

In addition, metal soaps (i.e. the salts of higher fatty acids with the exception of the alkali metal salts) are advantageous oil thickeners for the purposes of the present invention, such as, for example, aluminium stearate, zinc stearate and/or magnesium stearate.

The Pickering emulsions according to the invention can be used as a base for cosmetic or dermatological stick formulations. These can have the customary composition and be used, for example, for the treatment and care of the skin, as a lipcare product, as a deodorant product and as a make-up or make-up removal product in decorative cosmetics, or as a light protection preparation. In some instances it is possible and advantageous to use the compositions according to the invention as bases for pharmaceutical formulations.

For use, the cosmetic and dermatological preparations according to the invention are applied to the skin in a sufficient amount in the manner customary for cosmetics.

The cosmetic and dermatological preparations according to the invention can comprise dyes and/or colour pigments, particularly when they are in the form of decorative lipsticks, lip defining pencils, concealer sticks, kohl pencils, eyeliner pencils and/or eyebrow pencils. The dyes and colour pigments can be chosen from the corresponding positive list of the Cosmetics Directive or from the EU list of cosmetic colorants. In most cases, they are identical to the dyes permitted for foods. Advantageous colour pigments are, for example, titanium dioxide, mica, iron oxides (e.g. $Fe_2O_3$, $Fe_3O_4$, FeO(OH)) and/or zinc oxide. Advantageous dyes ar, for example, carmine, berlin blue, chrome oxide green, ultramarine blue and/or manganese violet. It is particularly advantageous to choose the dyes and/or colour pigments from the following list. The Colour Index Numbers (CIN) are taken from the *Rowe Colour Index*, 3rd edition, Society of Dyers and Colourists, Bradford, England, 1971.

| Chemical or other name | CIN | Colour |
| --- | --- | --- |
| Pigment Green | 10006 | green |
| Acid Green 1 | 10020 | green |
| 2,4-Dinitrohydroxynaphthalene-7-sulphonic acid | 10316 | yellow |
| Pigment Yellow 1 | 11680 | yellow |

| Chemical or other name | CIN | Colour |
|---|---|---|
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxy-naphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulphodiethylamido-1'-phenylazo)-3-hydroxy-5''-chloro-2'',4''-dimethoxy-2-naphthanilide | 12490 | red |
| Disperse Yellow 16 | 12700 | yellow |
| 1-(4-Sulpho-1-phenylazo)-4-aminobenzene-5-sulphonic acid | 13015 | yellow |
| 2,4-Dihydroxyazobenzene-4'-sulphonic acid | 14270 | orange |
| 2-(2,4-Dimethylphenylazo-5-sulpho)-1-hydroxy-naphthalene-4-sulphonic acid | 14700 | red |
| 2-(4-Sulpho-1-naphthylazo)-1-naphthol-4-sulphonic acid | 14720 | red |
| 2-(6-Sulpho-2,4-xylylazo)-1-naphthol-5-sulphonic acid | 14815 | red |
| 1-(4'-Sulphophenylazo)-2-hydroxynaphthalene | 15510 | orange |
| 1-(2-Sulpho-4-chloro-5-carboxy-1-phenylazo)-2-hydroxynaphthalene | 15525 | red |
| 1-(3-Methylphenylazo-4-sulpho)-2-hydroxy-naphthalene | 15580 | red |
| 1-(4',(8')-Sulphonaphthylazo)-2-hydroxynaphthalene | 15620 | red |
| 2-Hydroxy-1,2'-azonaphthalene-1'-sulphonic acid | 15630 | red |
| 3-Hydroxy-4-phenylazo-2-naphthylcarboxylic acid | 15800 | red |
| 1-(2-Sulpho-4-methyl-1-phenylazo)-2-naphthyl-carboxylic acid | 15850 | red |
| 1-(2-Sulpho-4-methyl-5-chloro-1-phenylazo)-2-hydroxynaphthalene-3-carboxylic acid | 15865 | red |
| 1-(2-Sulpho-1-naphthylazo)-2-hydroxynaphthalene-3-carboxylic acid | 15880 | red |
| 1-(3-Sulpho-1-phenylazo)-2-naphthol-6-sulphonic acid | 15980 | orange |
| 1-(4-Sulpho-1-phenylazo)-2-naphthol-6-sulphonic acid | 15985 | yellow |
| Allura Red | 16035 | red |
| 1-(4-Sulpho-1-naphthylazo)-2-naphthol-3,6-disulphonic acid | 16185 | red |
| Acid Orange 10 | 16230 | orange |
| 1-(4-Sulpho-1-naphthylazo)-2-naphthol-6,8-disulphonic acid | 16255 | red |
| 1-(4-Sulpho-1-naphthylazo)-2-naphthol-3,6,8-trisulphonic acid | 16290 | red |
| 8-Amino-2-phenylazo-1-naphthol-3,6-disulphonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulpho-1-phenylazo)-1-(4-sulphophenyl)-5-hydroxypyrazolone-3-carboxylic acid | 19140 | yellow |
| Pigment Yellow 16 | 20040 | yellow |
| 2,6-(4'-Sulpho-2'',4''-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulpho-1''-phenylazo)-7'-sulpho-1'-naphthylazo]-1-hydroxy-7-aminonaphthalene-3,6-disulphonic acid | 27755 | black |
| 4'-[(4''-Sulpho-1''-phenylazo)-7'-sulpho-1'-naphthylazo]-1-hydroxy-8-acetylaminonaphthalene-3,5-disulphonic acid | 28440 | black |
| Direct Orange 34, 39, 44, 46, 60 | 40215 | orange |
| Food Yellow | 40800 | orange |
| trans-β-Apo-8'-carotenaldehyde (C$_{30}$) | 40820 | orange |
| trans-Apo-8'-carotinic acid (C$_{30}$)-ethyl ester | 40825 | orange |
| Canthaxanthin | 40850 | orange |
| Acid Blue 1 | 42045 | blue |
| 2,4-Disulpho-5-hydroxy-4'-4''-bis(diethylamino)-triphenylcarbinol | 42051 | blue |
| 4-[(4-N-Ethyl-p-sulphobenzylamino)phenyl(4-hydroxy-2-sulphophenyl)(methylene)-1-(N-ethyl-N-p-sulphobenzyl)-2,5-cyclohexadienimine] | 42053 | green |
| Acid Blue 7 | 42080 | blue |
| (N-Ethyl-p-sulphobenzylamino)phenyl(2-sulphophenyl)methylene-(N-ethyl-N-p-sulphobenzyl)$^{2,5}$-cyclohexadienimine | 42090 | blue |
| Acid Green 9 | 42100 | green |
| Diethyldisulphobenzyldi-4-amino-2-chloro-di-2-methylfuchsonimmonium | 42170 | green |
| Basic Violet 14 | 42510 | violet |
| Basic Violet 2 | 42520 | violet |
| 2'-Methyl-4'-(N-ethyl-N-m-sulphobenzyl)amino-4''-(N-diethyl)amino-2-methyl-N-ethyl-N-m-sulphobenzylfuchsonimmonium | 42735 | blue |
| 4'-(N-Dimethyl)amino-4''-(N-phenyl)aminonaphtho-N-dimethylfuchsonimmonium | 44045 | blue |
| 2-Hydroxy-3,6-disulpho-4,4'-bisdimethylamino-naphthofuchsonimmonium | 44090 | green |
| Acid Red 52 | 45100 | red |
| 3-(2'-Methylphenylamino)-6-(2'-methyl-4'-sulphophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulphonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminium complex | 58000 | red |
| 3-Oxypyrene-5,8,10-sulphonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulpho-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulphonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6,19; Natural Red 1 | 75100 | yellow |
| Bixin, Norbixin | 75120 | orange |
| Lycopene | 75125 | yellow |
| trans-alpha-, beta- and gamma-carotene | 75130 | orange |
| Keto- and/or hydroxyl derivates of carotene | 75135 | yellow |
| Guanine or pearlizing agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and Chlorophyllins | 75810 | green |
| Aluminium | 77000 | white |
| Hydrated alumina | 77002 | white |
| Hydrous aluminium silicates | 77004 | white |
| Ultramarine | 77007 | blue |
| Pigment Red 101 ad 102 | 77015 | red |

-continued

| Chemical or other name | CIN | Colour |
|---|---|---|
| Barium sulphate | 77120 | white |
| Bismuth oxychloride and its mixtures with mica | 77163 | white |
| Calcium carbonate | 77220 | white |
| Calcium sulphate | 77231 | white |
| Carbon | 77266 | black |
| Pigment black 9 | 77267 | black |
| *Carbo medicinalis vegetabilis* | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide, hydrated | 77492 | yellow |
| Iron oxide | 77499 | black |
| Mixtures of iron (II) and iron (III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7\ H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavine | | yellow |
| Sugar colouring | | brown |
| Capsanthin, capsorubin | | orange |
| Betanin | | red |
| Benzopyrylium salts, Anthocyans | | red |
| Aluminium, zinc, magnesium and calcium stearate | | white |
| Bromothymol blue | | blue |
| Bromocresol green | | green |
| Acid Red 195 | | red |

If the stick formulations according to the invention are not in the form of lip(care) sticks, it is favourable to choose, as the dye, one or more substances from the following group: 2,4-dihydroxyazobenzene, 1-(2'-chloro-4'-nitro-1'-phenylazo)-2-hydroxynaphthalene, Ceres Red, 2-(4-sulpho-1-naphthylazo)-1-naphthol-4-sulphonic acid, calcium salt of 2-hydroxy-1,2'-azonaphthalene-1'-sulphonic acid, calcium and barium salts of 1-(2-sulpho-4-methyl-1-phenylazo)-2-naphthylcarboxylic acid, calcium salt of 1-(2-sulpho-1-naphthylazo)-2-hydroxynaphthalene-3-carboxylic acid, aluminium salt of 1-(4-sulpho-1-phenylazo)-2-naphthol-6-sulphonic acid, aluminium salt of 1-(4-sulpho-1-naphthylazo)-2-naphthol-3,6-disulphonic acid, 1-(4-sulpho-1-naphthylazo)-2-naphthol-6,8-disulphonic acid, aluminium salt of 4-(4-sulpho-1-phenylazo)-1-(4-sulphophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalone disulphonic acid, aluminium salt of indigo disulphonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are stick formulations with a content of pearlescent pigments. Preference is given in particular to the types of pearlescent pigments listed below:
1. Natural pearlescent pigments, such as, for example
   "Pearl essence" (guanine/hypoxanthin mixed crystals from fish scale) and
   "Mother of pearl" (ground mussel shells)
2. Monocrystalline pearlescent pigments, such as, for example, bismuth oxychloride (BiOCl)
3. Layer substrate pigments: e.g. mica/metal oxide Bases for pearlescent pigments are, for example, pulverulent pigments or castor oil dispersions of bismuth oxychloride and/or titanium dioxide, and bismuth oxichloride and/or titanium dioxide on mica. The lustre pigment listed under CIN 77163, for example, is particularly advantageous.

Also advantageous are, for example, the following types of pearlescent pigment based on mica/metal oxide:

| Group | Coating/layer thickness | Colour |
|---|---|---|
| Silver-white pearlescent pigments | $TiO_2$: 40–60 nm | silver |
| Interference pigments | $TiO_2$: 60–80 nm | yellow |
| | $TiO_2$: 80–100 nm | red |
| | $TiO_2$: 100–140 nm | blue |
| | $TiO_2$: 120–160 nm | green |
| Colour lustre pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/berlin blue | deep blue |
| | $TiO_2$/carmine | red |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("Ronaspheres"), which are marketed by Merck and are particularly suitable for the optical reduction of fine lines.

It can moreover be advantageous to dispense completely with a substrate such as mica. Particular preference is given to iron pearlescent pigments prepared without the use of mica. Such pigments are obtainable, for example, under the trade name Sicopearl Kupfer 1000 from BASF.

The dyes and pigments can be present either individually or in a mixture, and can be mutually coated with one another, differing coating thicknesses generally giving rise to different colour effects. The total amount of dyes and colour-imparting pigments is advantageously chosen from the range from, for example, 0.1% by weight to 30% by weight, preferably from 0.5 to 15% by weight, in particular from 1.0 to 10% by weight, in each case based on the total weight of the preparations.

The novel cosmetic and dermatological preparations may comprise cosmetic auxiliaries, as are customarily used in such preparations, e.g. preservatives, bactericides, perfumes, antifoams, pigments, thickeners, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives.

A surprising property of the novel preparations is that they are very good vehicles for cosmetic or dermatological active ingredients into the skin, advantageous active ingredients being antioxidants which are able to protect the skin against oxidative stress.

According to the invention, the preparations advantageously comprise one or more antioxidants. Antioxidants which are favourable, but nevertheless optional, are all antioxidants which are suitable or customary for cosmetic and/or dermatological applications. It is advantageous to use antioxidants as the sole active ingredient class when, for example, a cosmetic or dermatological application is at the fore, such as, for example, the control of oxidative stress of the skin. It is, however, also favourable to provide the novel stick preparations with a content of one or more antioxidants if the intention is for the preparations to serve another purpose, e.g. as deodorants or sunscreens.

The antioxidants are particularly advantageously chosen from the group consisting of amino acids (e.g. glycine, histidine, tyrosine, tryptophan) and derivatives thereof, imidazoles, (e.g. urocanic acid) and derivatives thereof, peptides, such as D,L-camosine, D-camosine, L-camosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to μmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, camosine, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, transstilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably from 0.001 to 30% by weight, particularly preferably from 0.05 to 20% by weight, in particular from 0.1 to 10% by weight, based on the total weight of the preparation.

If vitamin E and/or derivatives thereof are used as the antioxidant or antioxidants, their respective concentrations are advantageously chosen from the range from 0.001 to 10% by weight, based on the total weight of the formulation.

If vitamin A or vitamin A derivatives or carotenes or derivatives thereof are used as the antioxidant or antioxidants, their respective concentrations are advantageously chosen from the range from 0.001 to 10% by weight, based on the total weight of the formulation.

According to the invention, the active ingredients (one or more compounds) can also very advantageously be chosen from the group consisting of lipophilic active ingredients, in particular from the following group:

Acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular gamma-linolenic acid, oleic acid, eicosapentaenoic acid, docosahexaenoic acid and derivatives thereof, chloramphenicol, caffeine, prostaglandins, thymol, camphor, extracts or other products of vegetable or animal origin, for example evening primrose oil, starflower oil or currant seed oil, fish oils, cod-liver oil or also ceramides and ceramide-like compounds etc.

It is also advantageous to choose the active ingredients from the group of refatting substances, for example purcellin oil, Eucerit® and Neocerit®.

The list of specified active ingredients or active ingredient combinations which can be used in the Pickering emulsion sticks according to the invention is of course not intended to be limiting.

Cosmetic and dermatological stick preparations which are in the form of a sunscreen are also favourable. These preferably comprise at least one UV-A filter substance and/or at least one UV-B filter substance and/or at least one further inorganic pigment selected from the group consisting of the oxides of iron, zirconium, silicon, manganese, aluminium, cerium and mixtures thereof and also modifications in which the oxides are the active agents.

For the purposes of the present invention, it is, however, also advantageous to provide cosmetic and dermatological preparations whose main purpose is not protection against sunlight, but which nevertheless comprise substances which protect against UV. For example, UV-A and UV-B filter substances can be commonly incorporated into lip balm sticks.

The preparations according to the invention can advantageously comprise substances which absorb UV radiation in the UV-A and UV-B range, the total amount of filter substances being, for example, from 0.1% by weight to 30% by weight, preferably from 0.5 to 20% by weight, in particular from 1.0 to 15% by weight, based on the total weight of the preparations, in order to provide cosmetic sticks which protect the skin from the whole range of ultraviolet radiation. They can also be used as sunscreens for the skin.

Advantageous UV-A filter substances for the purposes of the present invention are dibenzoyl methane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Further advantageous UV-A filter substances are phenylene-1,4-bis(2-benzimidazyl)-3,3'-5,5'-tetrasulphonic acid:

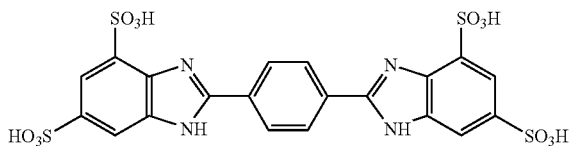

and its salts, particularly the corresponding sodium, potassium or triethanolammonium salts, in particular phenylene-1,4-bis-(2-benzimidazyl)-3,3'-5,5'-tetrasulphonic bis-sodium salt:

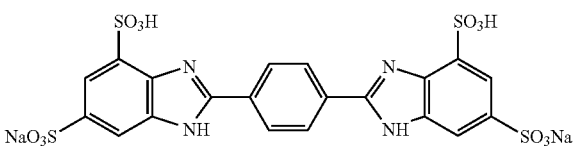

and 1,4-di(2-oxo-10-sulpho-3-bornylidenemethyl)benzene and salts thereof (in particular the corresponding 10-sulphato compounds, in particular the corresponding sodium, potassium or triethanolammonium salt), which is also referred to as benzene-1,4-di(2-oxo-3-bornylidenemethyl-10-sulphonic acid) and is characterized by the following structure:

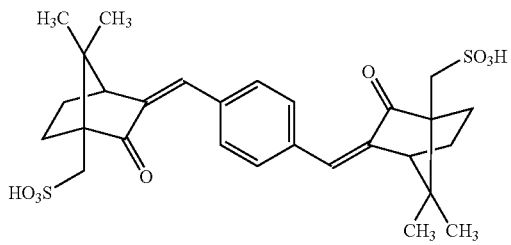

Advantageous UV filter substances for the purposes of the present invention are also broad-band filters, i.e. filter substances which absorb both UV-A and UV-B radiation.

Advantageous broad-band filters and/or UV-B filter substances are, for example, bisresorcinyltriazine derivates having the following structure:

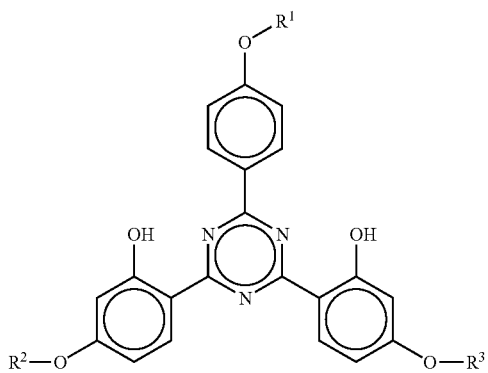

where $R^1$, $R^2$ and $R^3$ independently of one another are chosen from the group of branched and unbranched alkyl groups having 1 to 10 carbon atoms, or are a single hydrogen atom. Particular preference is given to 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH, and to tris(2-ethylhexyl) 4,4',4''-(1,3,5-triazine-2,4,6-triyltriimino)trisbenzoate, synonym: 2,4,6-tris[anilino(p-carbo-2'-ethyl-1'-hexyloxy)]-1,3,5-triazine (INCI: Octyl Triazone), which is marketed by BASF Aktiengesellschaft under the trade name UVINUL® T 150.

Other UV filter substances which have the structural formula

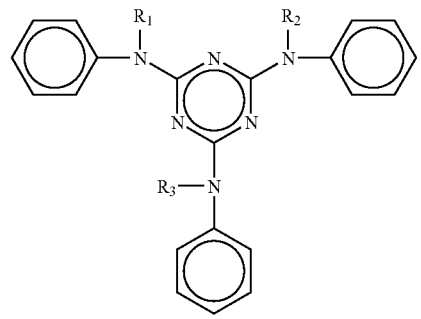

are also advantageous UV filter substances for the purposes of the present invention, for example the s-triazine derivatives described in European Laid-Open Specification EP 570 838 A1, whose chemical structure is given by the generic formula

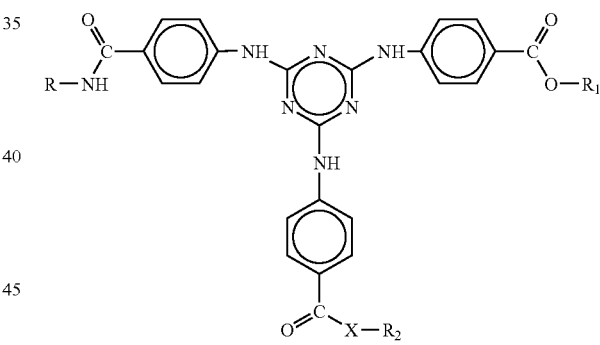

where
R is a branched or unbranched $C_1$–$C_{18}$-alkyl radical, a $C_5$–$C_{12}$-cycloalkyl radical, optionally substituted with one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

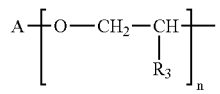

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted by one or more $C_1$–$C_4$-alkyl groups, when X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

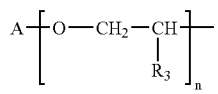

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, when X is an oxygen atom.

A particularly preferred UV filter substance for the purposes of the present invention is also an unsymmetrically substituted s-triazine, the chemical structure of which is given by the formula

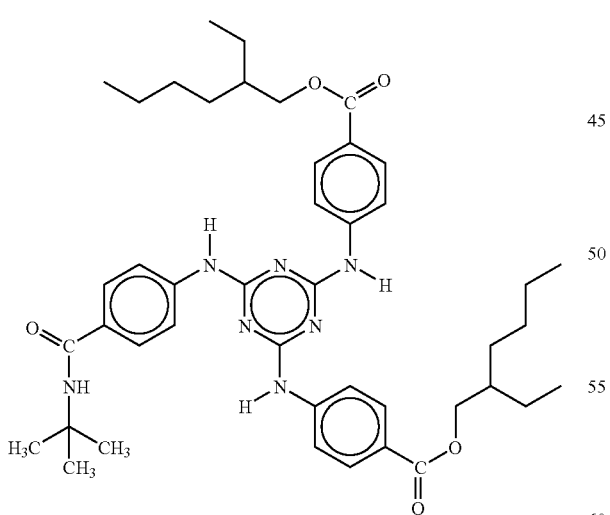

which is also referred to below as dioctylbutylamidotriazone (INCI: Dioctylbutamidotriazone) and is available under the trade name UVA-SORB HEB from Sigma 3V.

European Laid-Open Specification 775 698 also describes preferred bisresorcinyltriazine derivatives, the chemical structure of which is given by the generic formula

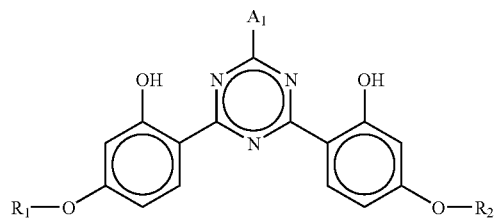

where $R_1$, $R_2$ and $A_1$ represent very different organic radicals.

Also advantageous for the purposes of the present invention are 2,4-bis{[4-(3-sulphonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethyl-carboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)-4-(1,1,3,3-tetramethylbutyl)phenol), which is characterized by the chemical structural formula

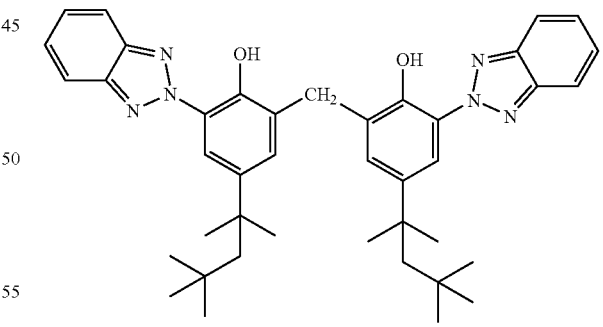

and is available under the trade name Tinosorb® M from CIBA-Chemikalien GmbH.

Another advantageous broad-band filter for the purposes of the present invention is 2-(2H-benzotriazol-2-yl)4-methyl-6-[2-methyl-3-[1,3,3,3-tetramethyl-1-[(trimethylsilyl)oxy]disiloxanyl]propyl]phenol (CAS No.: 155633-54-8) having the INCI name Drometrizole Trisiloxane, which is characterized by the chemical structural formula

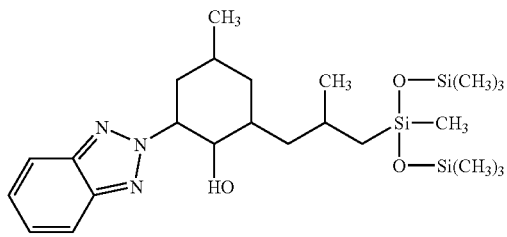

The UV-B filters can be oil-soluble or water-soluble. Examples of advantageous oil-soluble UV-B filter substances are:

- 3-benzylidenecamphor derivatives, preferably 3-(4-methylbenzylidene)camphor, 3-benzylidenecamphor;
- 4-aminobenzoic acid derivatives, preferably 2-ethylhexyl 4-(dimethylamino)benzoate, amyl 4-(dimethylamino) benzoate;
- 2,4,6-trianilino(p-carbo-2'-ethyl-1'-hexyloxy)-1,3,5-triazine;
- esters of benzalmalonic acid, preferably di(2-ethylhexyl) 4-methoxybenzalmalonate,
- esters of cinnamic acid, preferably 2-ethylhexyl 4-methoxycinnamate, isopentyl 4-methoxycinnamate;
- derivates of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Examples of advantageous water-soluble UV-B filter substances are:

- salts of 2-phenylbenzimidazole-5-sulphonic acid, such as its sodium, potassium or its triethanolammonium salt, and also the sulphonic acid itself;
- sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)sulphonic acid and salts thereof.

A further light protection filter substance which can be used advantageously according to the invention is ethylhexyl 2-cyano-3,3-diphenylacrylate (octocrylene), which is available from BASF under the name Uvinul N 539 and is characterized by the following structure:

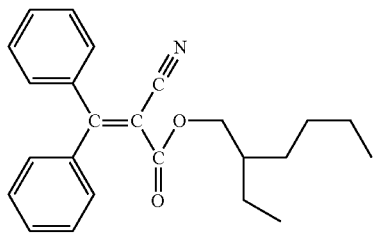

It can also be of considerable advantage to use polymer-bonded or polymeric UV filter substances in the preparations according to the present invention, in particular those described in WO-A-92/20690.

In some instances, it can also be advantageous to incorporate further UV-A and/or UV-B filters in accordance with the invention into cosmetic or dermatological preparations, for example certain salicylic acid derivatives, such as 4-isopropylbenzyl salicylate, 2-ethylhexyl salicylate (=octyl salicylate), homomenthyl salicylate.

The list of given UV filters which can be used for the purposes of the present invention is not of course intended to be limiting.

Preparations according to the invention can also be advantageously used as bases for cosmetic deodorants and antiperspirants, so that a particular embodiment of the present invention relates to Pickering emulsions as bases for cosmetic deodorant sticks.

Cosmetic deodorants are used to control body odour which arises when fresh perspiration, which is in itself odourless, is decomposed by microorganisms. Customary cosmetic deodorants are based on various modes of action.

In antiperspirants, astringents, mainly aluminium salts, such as aluminium hydroxychloride (aluminium chlorohydrate), reduce perspiration production.

The use of antimicrobial substances in cosmetic deodorants can reduce the bacterial flora on the skin. In an ideal situation, only the microorganisms which cause the odour should be effectively reduced. The flow of perspiration itself is not influenced as a result, and in ideal circumstances, only the microbial decomposition of perspiration is stopped temporarily.

The combination of astringents and antimicrobial active substances in one and the same composition is also common.

All active ingredients common for deodorants or antiperspirants can advantageously be used, for example odour masking agents, such as customary perfume constituents, odour-absorbers, for example the phyllosilicates described in German Laid-Open Specification DE 40 09 347, of these in particular montmorillonite, kaolinite, illite, beidellite, nontronite, saponite, hectorite, bentonite, smectite, and also, for example, zinc salts of ricinoleic acid. Antimicrobial agents are also suitable to be incorporated into the W/O emulsion sticks according to the invention. Advantageous substances are, for example, 2,4,4'-trichloro-2'-hydroxy diphenyl ether (Irgasan), 1,6-di(4-chlorophenylbiguanido) hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol) and also the active ingredients or active ingredient combinations described in DE-A-37 40 186, DE-A-39 38 140, DE-A42 04 321, DE-A-42 29 707, DE-A-43 09 372, DE-A44 11 664, DE-A-195 41 967, DE-A-195 43 695, DE-A-195 43 696, DE-A-195 47 160, DE-A-196 02 108, DE-A-196 02 110, DE-A-196 02 111, DE-A-196 31 003, DE-A-196 31 004 and DE-A-196 34 019, and the patent specifications DE-42 29 737, DE-42 37 081, DE-43 24 219, DE-44 29 467, DE-44 23 410 and DE-195 16 705. Sodium hydrogencarbonate can also be used advantageously.

The list of specified active ingredients and active ingredient combinations which can be used in the Pickering emulsion sticks according to the invention is of course not intended to be limiting.

The cosmetic deodorants according to the invention can be in the form of aqueous, cosmetic sticks which can be applied from normal containers.

The amount of antiperspirant active ingredients or deodorants (one or more compounds) in the preparations is preferably from 0.01 to 30% by weight, particularly preferably, from 0.1 to 20% by weight, in particular 1–10% by weight, based on the total weight of the preparation.

The sticks according to the invention are additionally excellent vehicles for dermatological active ingredients. In particular, they are suitable as carriers for substances effective against acne. Acne is a skin disorder with many forms and causes, characterized by noninflamed and inflamed bumps, originating from blocked hair follicles (comedones) which can lead to the formation of pustules, abscesses and scars. The most frequent is Acne vulgaris, which occurs predominantly in puberty. Causative conditions for Acne vulgaris are the keratinization and blocking of the hair follicle opening, the production of sebum, which is dependent on the level of male sex hormones in the blood, and the production of free fatty acids and tissue-damaging enzymes by bacteria (*Propionibacterium acnes*).

It is therefore advantageous to add to the preparations according to the invention, substances which are effective against acne, for example against *Propionibacterium acnes* (for example those described in DE-A 42 29 707, DE-A 43 05 069, DE-A 43 07 976, DE-A 43 37 711, DE-A 43 29 379) but also other substances which are effective against acne, for example all-trans-retinoic acid, 13-cis-retinoic acid and related substances or anti-inflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol and antibiotics and/or keratolytics.

Keratolytics are substances which soften keratinized skin (such as, for example, warts, corns, calluses and the like) so that it can be removed more easily or so that it falls off or peels off.

All of the common substances effective against acne can be used advantageously, in particular benzoyl peroxide, bituminosulphonates (ammonium, sodium and calcium salts of shale oil sulphonic acids), salicylic acid (2-hydroxybenzoic acid), miconazole (1-[2-(2,4-dichlorobenzyloxy)-2-(2,4-dichlorophenyl)ethyl]imidazole) and derivatives, adapalene (6-[3-(1-adamantyl)-4-methoxyphenyl]-2-naphthoic acid), azelaic acid (nonanedioic acid), mesulfen (2,7-dimethylthianthrene, $C_{14}H_{12}S_2$) and aluminium oxide, zinc oxide and/or finely dispersed sulphur.

The amount of anti-acne agents (one or more compounds) in the preparations is preferably from 0.01 to 30% by weight, particularly preferably 0.1–20% by weight, in particular 1–10% by weight, based on the total weight of the preparation.

W/O Pickering emulsion sticks according to the invention are obtainable by firstly dispersing the pigments in the fatty phase, and then combining the fatty phase with the aqueous phase.

The invention thus also provides a method for the preparation of the Pickering emulsion sticks according to the invention, which is characterized in that the modified phyllosilicate particles are dispersed in a manner known per se in the fatty phase, which comprises from 10 to 70% by weight, based on the weight of the fatty phase, of fatty and/or wax components which melt above a temperature of 40° C., and, if desired, cosmetic or pharmaceutical auxiliaries, additives and/or active ingredients, with uniform stirring and optionally with heating, and, during the homogenization operation, the water phase, which, if desired, likewise comprises cosmetic or pharmaceutical auxiliaries, additives and/or active ingredients, is mixed with the fatty phase.

The examples below serve to illustrate the present invention without limiting it. The numerical values in the examples mean percentages by weight, based on the total weight of the respective preparations.

EXAMPLES

| | % by weight |
|---|---|
| 1. Moisturizing lipstick | |
| Carnauba wax | 1.5 |
| Candelilla wax | 4 |
| Beeswax | 2 |
| Microcrystalline wax | 1 |
| Jojoba oil | 3 |
| Lanolin oil | 3 |
| CI 77891 (TiO$_2$) | 3 |
| CI 15880:1 (D&C Red 7) | 2.3 |
| CI 73360 (D&C Red 30) | 0.7 |
| Quaternium-18 hectorite (bentone 38) | 0.5 |
| Tocopherol | 0.1 |
| Lecithin | 0.5 |
| Glycerol | 3 |
| Water | 50 |
| Perfume, preservatives, antioxidants | q.s. |
| *Ricinus communis* | ad 100 |
| 2. Lipstick containing ceramide | |
| Stearyl alcohol | 2 |
| Behenyl alcohol | 2 |
| Ceramide 3 | 0.2 |
| C18–C38 Alkylhydroxystearoyl stearate | 4 |
| Candelilla wax | 4 |
| Shea butter | 4 |
| Lanolin oil | 8 |
| Macadamia oil | 8 |
| CI 15880:1 (D&C Red 7) | 2 |
| CI 17200 (D&C Red 33) | 1.5 |
| CI 42010:2 (FD&C Blue 1) | 0.5 |
| CI 77163 (BiOCl) | 3 |
| Quaternium-18 bentonite | 0.4 |
| Tromethamine magnesium aluminium silicate (Veegum Pro, Vanderbilt) | 0.1 |
| Panthenol | 5 |
| Water | 40 |
| Perfume, preservatives, antioxidants | q.s. |
| *Ricinus communis* | ad 100 |
| 3. Lipstick with high coverage | |
| Jojoba oil | 10 |
| Isopropyl palmitate | 5 |
| Eucerite | 0.3 |
| C$_{20}$–C$_{40}$ Alcohols (Luzatto & Figlio) | 3 |
| Carnauba wax | 2.8 |
| Candelilla wax | 4.2% |
| Beeswax | 2.8 |
| Microcrystalline wax | 2.8 |
| Polyethylene | 2 |
| CI 77891 (TiO$_2$) | 3 |
| CI 45380 (D&C Red 21) | 0.8 |
| CI 45380:3 (D&C Red 22) | 3 |
| CI 45410:2 (D&C Red 28) | 2.5 |
| Silica and mica (Micronasphere M, Merck) | 5 |
| Stearalkonium hectorite | 0.3 |
| Water | 30 |
| Perfume, preservative, antioxidants | q.s. |
| *Ricinus communis* | ad 100 |
| 4. Long-lasting lipstick | |
| Dimethicone copolyol candelilla | 7 |
| Microcrystalline wax | 8 |
| Hydrogenated polyisobutene (Polysnylan, Nippon) | 6 |
| C$_{18-38}$ Alkylhydroxystearoyl stearate | 1 |
| Cyclomethicone (DC 344, Dow Corning) | 28 |
| Methicone and TiO$_2$ (methicone treated TiO$_2$, US Cosmetics) | 4 |
| Boron nitride (Belsil BNP, Wacker) | 5 |
| CI 17200 (D&C Red 33) | 1.5 |
| CI 45380:3 (D&C Red 22) | 2 |
| Octyl salicylate | 2 |
| Octyl methoxycinnamate | 2 |
| Quaternium-18 hectorite | 0.5 |

-continued

| | % by weight |
|---|---|
| Water | 40 |
| Perfume, preservatives, antioxidants | q.s. |
| 5. Lip gloss | |
| Dimethicone copolyol candelilla | 8.5 |
| Microcrystalline wax | 6 |
| Squalane | 6 |
| $C_{18-38}$ Alkylhydroxystearoyl stearate | 1.5 |
| Lanolin oil | 5 |
| *Brassica campestris/Aleurites fordi* oil (Glossamer L-6600, Tri-K) | 10 |
| CI 45410:2 (D&C Red 28) | 1.8 |
| CI 45370:2 (D&C Orange 5) | 0.6 |
| CI 77492 (Iron oxide, yellow) | 2 |
| Iron oxide with aluminium and manganese oxide (Sicopearl, BASF) | 3 |
| Octyl salicylate | 2 |
| Water | 30 |
| Quaternium-18 hectorite | 0.5 |
| Perfume, preservatives, antioxidants | q.s. |
| *Ricinus communis* | ad 100 |
| 6. Lipstick free from mineral oil | |
| Macadamia oil | 18 |
| Octyldodecanol | 8 |
| Beeswax | 8 |
| Cetyl palmitate | 2 |
| Jojoba oil | 5 |
| Carnauba wax | 2 |
| Tocopherol acetate | 0.75 |
| CI 77891 ($TiO_2$) | 1.8 |
| CI 45380 (D&C Red 21) | 0.8 |
| CI 45380:3 (D&C Red 22) | 2.2 |
| CI 45410:2 (D&C Red 28) | 1.6 |
| Silica and mica (Micronasphere M, Merck) | 5 |
| Water | 50 |
| Quaternium-18 hectorite | 0.5 |
| Perfume, preservatives, antioxidants | q.s. |
| Squalane | ad 100 |
| 7. Lustre foundation stick | |
| Carnauba wax | 1.8 |
| Beeswax | 1.2 |
| Ozokerite | 0.8 |
| Stearyl methicone (Belsil SM 6018, Wacker) | 1.5 |
| Dimethicone | 8 |
| Petrolatum | 2 |
| Isostearyl isostearate | 5 |
| Silica coated with $TiO_2$ and $Fe_2O_3$ (Ronaspheres LDP, Merck) | 5 |
| Titanium dioxide (and) mica (Timiron, Merck) | 2 |
| Quaternium-18 hectorite | 0.8 |
| Glycerol | 3 |
| Perfume, preservatives, antioxidants | q.s. |
| Water | ad 100 |
| 8. Matt foundation stick | |
| Dimethicone/vinyl dimethicone crosspolymer | 2 |
| Hydrolyzed beeswax | 0.5 |
| Hydrogenated Jojoba oil | 2 |
| Stearyl methicone (Belsil SM 6018, Wacker) | 1.5 |
| Dimethicone | 8 |
| Shea butter | 3 |
| Isostearyl isostearate | 5 |
| $TiO_2$ | 1.5 |
| Kaolin | 1.2 |
| CI 77491 (Iron oxide red) | 0.3 |
| CI 77492 (Iron oxide yellow) | 0.6 |
| CI 77499 (Iron oxide black) | 0.15 |
| Nylon-12 (Orgasol Number, Elf Atochem) | 0.8 |
| Octyl salicylate | 2 |
| Octyltriazone (Uvinul T 150) | 2 |
| t-Butylmethoxydibenzoylmethane (Parsol 1789) | 1 |
| Glycerol | 5 |
| Quaternium-18 hectorite | 1 |
| EDTA | 0.5 |

-continued

| | % by weight |
|---|---|
| Perfume, preservatives, antioxidants | q.s. |
| Water | ad 100 |
| 9. Sunscreen stick | |
| Octyldodecanol | 10 |
| $C_{12-15}$ Alkyl benzoate | 15 |
| Octyltriazone | 2 |
| 4-Methylbenzylidenecamphor | 2 |
| Butylmethoxydibenzoylmethane | 2 |
| Vitamin E acetate | 0.5 |
| Preservative | 0.5 |
| Beeswax | 8 |
| Carnauba wax | 2 |
| Bentone 38 (Quaternium-18 hectorite) | 0.75 |
| Glycerol | 10 |
| Phenylbenzimidazolesulphonic acid | 2 |
| NaOH (45% strength solution in water) | 0.7 |
| Water | 40 |
| Caprylic/capric triglyceride | ad 100 |
| 10. Micropigment stick | |
| Octyldodecanol | 10 |
| Dicaprylyl ether | 10 |
| Vitamin E-acetate | 0.5 |
| Preservatives | 0.5 |
| Kester wax K82H ($C_{20-40}$ alkyl stearate) | 8 |
| Carnauba wax | 4 |
| Vaseline | 5 |
| Bentone 38 (Quaternium-18 hectorite) | 0.3 |
| Titanium dioxide | 5 |
| Zinc oxide | 5 |
| Glycerol | 10 |
| Water | 30 |
| Caprylic/capric triglyceride | ad 100 |
| 11. Deodorant stick | |
| Caprylic/capric triglyceride | 15 |
| Octyldodecanol | 10 |
| Dicaprylyl ether | 5 |
| Glyceryl monolaurate | 0.5 |
| Kester wax K82H ($C_{20-40}$ alkyl stearate) | 15 |
| Bentone 38 (quaternium-18 hectorite) | 1 |
| Glycerol | 5 |
| Aluminium chlorohydrate | 5 |
| Water | 35 |
| *Ricinus communis* | ad 100 |

What is claimed is:

1. Cosmetic or dermatological stick preparation, which is a finely disperse water-in-oil emulsion, comprising
    a) an oil phase which comprises from 10 to 70% by weight, based on the weight of the oil phase, of fatty and/or wax components which melt above a temperature of 40° C.,
    b) a water phase,
    c) at least one modified phyllosilicate pigment particles which exhibits both hydrophilic and lipophilic properties, which thus has amphiphilic character and positions itself at the water/oil interface, and
    d) at most 0.5% by weight, based on the total weight of the preparations, of one or more emulsifiers.

2. Preparation according to claim 1, wherein it is emulsifier-free.

3. Preparation according to claim 1, wherein the water phase content is from 15 to 60% by weight, based on the total weight of the preparations.

4. Preparation according to claim 1, wherein further cosmetic or pharmaceutical auxiliaries, additives and/or active ingredients are present.

5. Preparation according to claim 1 or 4, wherein the content of modified phyllosilicate pigment particles used is between 0.1% by weight and 30% by weight, based on the total weight of the preparations.

6. Preparation according to claim 1 or 4, wherein the modified phyllosilicate pigment particle(s) is/are chosen from the group which includes modified smectites, modified bentonites, modified montmorillonites and modified hectorites.

7. Preparation according to claim 6, wherein the modified phyllosilicate pigment particle(s) is/are a modified hectorite selected from the group consisting of stearalkonium hectorite and quaternium-18 hectorite.

8. Preparation according to claim 1 or 4, wherein, in addition to one or more modified phyllosilicate pigment particle(s), (a) further pigment(s) are present which are selected from the group consisting of modified polysaccharide, microfine polymer particles, boron nitride and micronized, inorganic pigments where the pigments can be present either individually or in a mixture.

9. Preparation according to claim 8, wherein the micronized, inorganic pigments is/are an amphiphilic metal oxide(s).

10. Preparation according to claim 9, wherein the amphiphilic metal oxide(s) are selected from the group consisting of titanium dioxide, zinc oxide, iron oxides or iron mixed oxides, silicon dioxide and silicates.

11. Preparation according to claim 1 or 4, wherein it is in the form of a make-up and/or cosmetic stick, and additionally comprises at least one dye and/or one color pigment.

12. Preparation according to claim 11, wherein the make-up and/or cosmetic stick form is selected from the group consisting of eyebrow pencil, kohl pencil, eyeshadow pencil, eyeliner pencil, concealer stick, powder stick and lipstick.

13. Preparation according to claim 1 or 4, wherein it comprises one or more additives or active ingredients selected from the group consisting of astringents, antioxidants, UV filter substances, antimicrobial substances and substances effective against acne.

14. Method for the preparation of Pickering emulsion sticks, wherein modified phyllosilicate pigment particles are dispersed in the oil phase, which comprises from 10 to 70% by weight, based on the weight of the oil phase, of fatty and/or wax components which melt above a temperature of 40° C., and, optionally, cosmetic or pharmaceutical auxiliaries, additives and/or active ingredients, with uniform stirring and optionally with heating, and, during the uniform stirring, the water phase, which, optionally comprises cosmetic or pharmaceutical auxiliaries, additives and/or active ingredients, is mixed with the oil phase.

15. A method of treating the skin comprising applying to the skin a preparation according to claim 1.

16. Cosmetic or dermatological stick preparation, which is a finely disperse water-in-oil emulsion, consisting essentially of
   a) an oil phase which comprises from 10 to 70% by weight, based on the weight of the oil phase, of fatty and/or wax components which melt above a temperature of 40° C.,
   b) a water phase,
   c) at least one modified phyllosilicate pigment particles which exhibits both hydrophilic and lipophilic properties, which thus has amphiphilic character and positions itself at the water/oil interface, and
   d) at most 0.5% by weight, based on the total weight of the preparations, of one or more emulsifiers.

* * * * *